United States Patent [19]

Dawson et al.

[11] 4,439,614
[45] Mar. 27, 1984

[54] 5,6-METHANO-5,6-DIHYDRORETINOIDS

[75] Inventors: Marcia I. Dawson, Los Altos; Rebecca Chan, Palo Alto; Peter D. Hobbs, Woodside, all of Calif.

[73] Assignee: SRI International, Menlo Park, Calif.

[21] Appl. No.: 421,065

[22] Filed: Sep. 22, 1982

[51] Int. Cl.³ .................... C07C 69/76; C07C 69/74
[52] U.S. Cl. ........................................ 560/8; 560/119; 562/501; 562/405; 568/374; 568/445; 568/819; 424/308; 424/298; 424/315; 564/123
[58] Field of Search ................. 560/119; 562/8, 501, 562/405; 564/123; 424/308, 305, 298

[56] References Cited

U.S. PATENT DOCUMENTS

| | | | |
|---|---|---|---|
| 2,917,523 | 12/1959 | Rommer | 260/410.9 R |
| 3,781,314 | 12/1973 | Bollag et al. | 260/410.9 R |
| 3,845,088 | 10/1974 | Findlay | 260/410.9 R |
| 3,931,257 | 1/1976 | Pawson | 260/408 |
| 4,044,051 | 8/1977 | Bollag et al. | 424/308 |
| 4,054,589 | 10/1977 | Bollag et al. | 260/408 |
| 4,081,470 | 3/1978 | Schleich | 260/410.9 |
| 4,147,708 | 4/1979 | Manchand | 260/413 |
| 4,163,103 | 7/1979 | Bollag et al. | 542/427 |
| 4,190,594 | 2/1980 | Gandes | 260/404 |
| 4,193,931 | 3/1980 | Loeliger | 424/308 |

OTHER PUBLICATIONS

Dawson; M. I. et al., J. Med. Chem. 1981; 24 1214–1223.
Boutwell, R. K. et al., Advances in Enzyme Regulation, vol. 17, Ed. Weber, G. Pergammon Press (1979).
Verma, A. K. et al., Cancer Res. (1979), 39:419–427.
Dawson, M. I. et al., J. Med. Chem. (1980), 23 1013–1022.
Dawson, M. I. et al., J. Med. Chem. (1981), 24:583–592.

*Primary Examiner*—Paul J. Killos
*Attorney, Agent, or Firm*—Ciotti & Murashige

[57] ABSTRACT

5,6-Methano-5,6-dihydroretinoids such as ethyl (E)-5,6-methano-5,6-dihydroretinoate and (E)-1-(4-carbethoxyphenyl)-2-methyl-4-(2,2,6-trimethylbicyclo[4.1.0]hept-1-yl)-1,3-butadiene are disclosed. These componds are useful as chemopreventive agents for inhibiting tumor promotion in epithelial cells and for treating nonmalignant skin disorders.

12 Claims, No Drawings

5,6-METHANO-5,6-DIHYDRORETINOIDS

REFERENCE TO GOVERNMENT GRANT OR CONTRACT

The invention described herein was made in the course of work under grant or contract from the National Institute of Health.

DESCRIPTION

1. Technical Field

The invention is in the fields of retinoid chemistry and chemotherapy. More particularly, the invention relates to 5,6-methano-5,6-dihydroretinoids.

2. Background Art

The progressive loss of the regulation of cellular differentiation by epithelial cells can result in cancer. Retinoic acid and some of its analogues (retinoids) have been investigated as "chemopreventive" agents, that is, agents that interfere with tumor promotion in epithelial cells. Boutwell, R. K.; et al, Advances in Enzyme Regulation, V.17, Ed. Weber, G., Pergamon Press (1979); Verma, A. K.; et al, Cancer Res (1979) 39:419–427; Dawson, M. I.; et al, J Med Chem (1980) 23:1013–1022 and J Med Chem (1981) 24:583–582. Included among these retinoids are 5,6-epoxy-5,6-dihydroretinoic acid—a metabolite of retinoic acid—and (E)-1-(4-carbethoxy)-2-methyl-4-(1,2-epoxy-2,6,6,-trimethylcyclohex-1-yl)-1,3-butadiene. Both of these epoxides exhibited biological activity in the ornithine decarboxylase (ODC) assay, Verma, A. K., and Boutwell, R. K. Cancer Res (1977) 37:2196–2201 which measures a compound's ability to inhibit tumor promotion as a function of the compound's effect on ODC induction in mouse epidermis by tumor-promoting phorbol esters.

An object of the present invention is to provide novel retinoids in which the $5,6_R$ (the subscript R indicates use of the retinoid numbering system) double bond of the β-cyclogeranylidene ring has been replaced with a cylopropyl ring. The metabolic deactivation of these retinoids is reduced relative to analogues in which the $5,6_R$ double bond of the ring is not modified. Such deactivation allows these novel retinoids to be administered at reduced dosages.

DISCLOSURE OF THE INVENTION

The compounds of the invention are 5,6-methano-5,6-dihydroretinoids of the following formula:

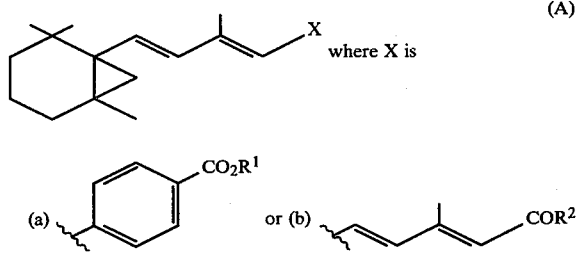

where X is and $R^1$ is hydrogen, alkyl or aryl and $R^2$ is hydroxyl, alkoxy or $NR^3R^4$ where $R^3$ is hydrogen, alkyl, or aryl and $R^4$ is alkyl or aryl, and the 13-cis isomers of the retinoids defined by formula (A) where X is (b).

When used as pharmaceutical agents one or more of these 5,6-methano-5,6-dihydroretinoids is combined with a suitable pharmaceutically acceptable carrier and an effective dose thereof is administered to the patient.

MODES FOR CARRYING OUT THE INVENTION

The alkyl group represented by $R^1$ may be straight chain or branched chain. It will typically contain 1 to about 8 carbon atoms, preferably 1 to 4 carbon atoms. Examples of such alkyl groups are methyl, ethyl, propyl, isopropyl, n-butyl, sec-butyl, n-amyl, n-hexyl, 2-methylamyl, n-heptyl, 3-methyl-hexyl, and n-octyl. The aryl group represented by $R^1$ is preferably mononuclear. The aryl group will usually contain 6 to 15 carbon atoms, more usually 6 to 10 carbon atoms. Examples of aryl groups that $R^1$ may represent are phenyl, tolyl, cumyl, xylyl, benzyl, naphthyl, and the like. Phenyl is a particularly preferred aryl group.

The alkoxy group represented by $R^2$ may be straight chain or branched chain and will usually contain 1 to about 8 carbon atoms, preferably 1 to 4 carbon atoms. Examples of such alkoxy groups are methoxy, ethoxy, isopropoxy, butoxy, hexoxy, heptoxy and octoxy.

The alkyl groups ($R^3$ and $R^4$) of the amides represented by formula (A) may also be straight chain or branched chain. They will typically each contain 1 to 8 carbon atoms, preferably 1 to 4 carbon atoms and have 0 or 1 hydroxy substituent. Examples of such alkyl groups are those mentioned above and hydroxy methyl, 2-hydroxyethyl, 3-hydroxypropyl, 2-hydroxyhexyl, and the like. The corresponding aryl groups represented by $R^3$ and/or $R^4$ may be substituted or unsubstituted mononuclear or polynuclear moieties. The substituents will usually be lower (ie, 1 to 4 carbon atoms) alkyl, lower alkoxy, or hydroxy. When substituted, the group will usually be mono-substituted. Examples of such groups are phenyl, o-, m-, or p-hydroxyphenyl, o-, m-, or p-methoxyphenyl, ethylbenzyl, cumyl, naphthyl, phenanthryl, azulyl, and the like. These aryl groups will typically contain 6 to about 15 carbon atoms. Phenyl, 4-hydroxyphenyl, and 4-methoxyphenyl are preferred aryl groups.

Representative examples of 5,6-methano-5,6-dihydroretinoids of formula (A) are (E)-5,6-methano-5,6-dihydroretinoic acid, methyl (E)-5,6-methano-5,6-dihydroretinoate, ethyl (E)-5,6-methano-5,6-dihydroretinoate, propyl (E)-5,6-methano-5,6-dihydroretinoate, isopropyl (E)-5,6-methano-5,6-dihydroretinoate, butyl (E)-5,6-methano-5,6-dihydroretinoate, sec.butyl (E)-5,6-methano-5,6-dihydroretinoate, hexyl (E)-5,6-methano-5,6-dihydroretinoate, heptyl (E)-5,6-methano-5,6-dihydroretinoate, isooctyl (E)-5,6-methano-5,6-dihydroretinoate, octyl (E)-5,6-methano-5,6-dihydroretinoate, N-methyl (E)-5,6-methano-5,6-dihydroretinamide, N-(2-hydroxyethyl) (E)-5,6-methano-5,6-dihydroretinamide, N-isopropyl (E)-5,6-methano-5,6-dihydroretinamide, N-butyl (E)-5,6-methano-5,6-dihydroretinamide, N-hexyl (E)-5,6-methano-5,6-dihydroretinamide, N-octyl (E)-5,6-methano-5,6-dihydroretinamide, N,N-dimethyl (E)-5,6-methano-5,6-dihydroretinamide, N-ethyl-N-methyl (E)-5,6-methano-5,6-dihydroretinamide, N-(2-hydroxyethyl)-N-methyl (E)-5,6-methano-5,6-dihydroretinamide, N-methyl-N-octyl (E)-5,6-methano-5,6-dihydroretinamide, N-phenyl (E)-5,6-methano-5,6-dihydroretinamide, N-(4-hydroxyphenyl) (E)-5,6-methano-5,6-dihydroretinamide, N-(4-methoxyphenyl) (E)-5,6-methano-5,6-dihydroretinamide, N-methyl-N-phenyl (E)-5,6-methano-5,6-dihydroretinamide, N-naphthyl (E)-5,6-methano- 5,6-dihydroretinamide, N-tolyl (E)-5,6-methano-5,6-dihydroretinamide, (E)-1-(4-carboxyphenyl-2-methyl-4-(2,2,6-trimethylbicyclo[4.1.0]hept-1-yl)-1,3-butadiene, (E)-1-(4-carbmethoxyphenyl-2-methyl-4-(2,2,6-trimethylbicyclo[4.1.0]hept-1-yl)-1,3-butadiene, (E)-1-(4-carbethoxyphenyl)-2-methyl-4-(2,2,6-trimethylbicyclo[4.1.0]hept-1-yl)-1,3-butadiene, (E)-1-(4-carbpropoxyphenyl)-2-methyl-4-(2,2,6-trimethylbicyclo[4.1.0]hept-1-yl)-1,3-butadiene, (E)-1-(4-carbisopropoxyphenyl)-2-methyl-4-(2,2,6-trimethylbicyclo[4.1.0]hept-1-yl)-1,3-butadiene, (E)-1-(4-carbbutoxyphenyl)-2-methyl-4-(2,2,6-trimethylbicyclo[4.1.0]hept-1-yl)-1,3-butadiene, (E)-1-(4-carbpentoxyphenyl)-2-methyl-4-(2,2,6-trimethylbicyclo[4.1.0]hept-1-yl)-1,3-butadiene, (E)-1-(4-carbhexoxyphenyl)-2-methyl-4-(2,2,6-trimethylbicyclo[4.1.0]hept-1-yl)-1,3-butadiene, (E)-1-(4-carbheptoxyphenyl)-2-methyl-4-(2,2,6-trimethylbicyclo[4.1.0]hept-1-yl)-1,3-butadiene, (E)-1-(4-carboctoxyphenyl)-2-methyl-4-(2,2,6-trimethylbicyclo[4.1.0]hept-1-yl)-1,3-butadiene, (E)-1-(4-carbphenoxyphenyl)-2-methyl-4-(2,2,6-trimethylbicyclo[4.1.0]hept-1-yl)-1,3-butadiene, (E)-1-(4-carbbenzoxyphenyl)-2-methyl-4-(2,2,6-trimethylbicyclo[4.1.0]hept-1-yl)-1,3-butadiene, (E)-1-(4-carbnaphthoxyphenyl)-2-methyl-4-(2,2,6-trimethylbicyclo[4.1.0]hept-1-yl)-1,3-butadiene, and (E)-1-(4-carbisopropylphenoxyphenyl)-2-methyl-4-(2,2,6-trimethylbicyclo[4.1.0]hept-1-yl)-1,3-butadiene.

The reaction scheme for preparing the retinoids of formula (A) wherein X represents a substituted phenyl group is given below.

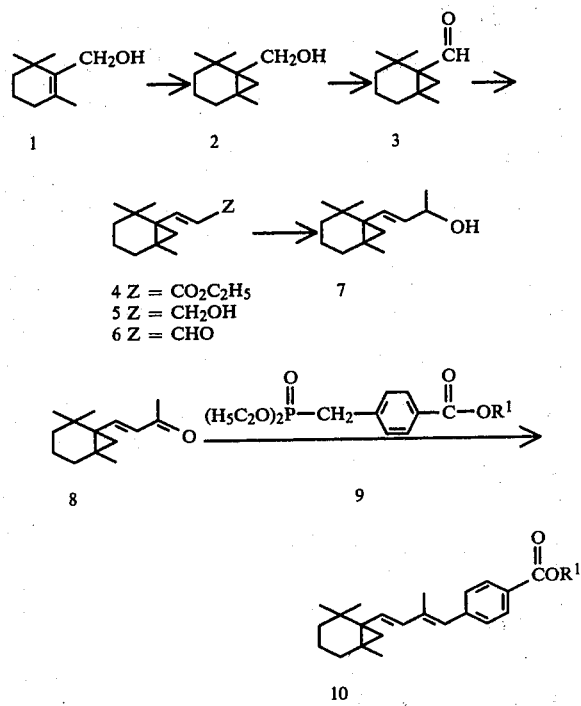

where $R^1$ is as described previously.

This scheme was used to make (E)-1-(4-carbethoxyphenyl)-2-methyl-4-(2,2,6-trimethylbicyclo[4.1.0]hept-1-yl)-1,3-butadiene as follows. The abbreviations used in the following description have the following meanings:

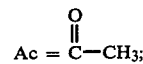

Et=ethyl; Bu=butyl; NMR=nuclear magnetic resonance; TLC=thin layer chromatography; IR=infrared; THF=tetrahydrofuran; 9-BBN=9-borabicyclo[3.3.1]nonane; DIBAL=diisobutylaluminum hydride; Me=methyl; LC=high performance liquid chromatography. The reference numerals are those indicated in the scheme.

Preparation of (2,2,6-trimethylbicyclo[4.1.0]hept-1-yl)methanol (2).

A solution of 0.4 g of $Cu(OAc)_2 \cdot H_2O$ in 20 mL of hot HOAc was treated with 8.8 g (0.13 g-atom) of Zn dust with shaking for 3 min, and the acid was decanted. The Zn-Cu couple was washed by decantation with 30 mL of 1:1 HOAc/$Et_2O$, followed by $Et_2O$ (6×30 mL). Next, 20 mL of $Et_2O$ was added together with a crystal of $I_2$. A mixture of 18.8 g (70 mmol) of $CH_2I_2$ and 3.08 g (20 mmol) of β-cyclogeraniol (1) was added dropwise over a 20-min period, with warming to maintain a gentle reflux. Heating at reflux was continued for an additional 2 h. The cooled solution was decanted, the residue was washed with $Et_2O$, and the total $Et_2O$ volume was brought to 200 mL. The solution was cooled in ice/$H_2O$, and pyridine (8 to 9 mL) was added dropwise until no further $ZnI_2$-pyridine complex separated. The reaction was cooled to −5° C. overnight, filtered twice, and evaporated. Further complex separated on evaporation. TLC (9:1 hexane/EtOAc) demonstrated a single product. The crude oil was eluted through a 3×25 cm silica gel column by 9:1 hexane/$Et_2O$, followed by 1:1 hexane/$Et_2O$. The spectrally pure, colorless oil weighed 3.4 g (quant): IR (film) 3400 (OH), 1460, 1385, 1365, 1155, 1035, 1010, 705 $cm^{-1}$; $^1H$ NMR ($CDCl_3$) δ0.22 (d, J=4.5 Hz, 1, cyclopropyl H), 0.49 (d, J=4.5 Hz, 1, cyclopropyl H), 0.99 (s, 3, $CH_3$), 1.21 (s, 3, $CH_3$), 1.26 (s, 3, $CH_3$), 1.0–1.8 [m, 7, $(CH_2)_3$, OH], 3.51 and 3.92 (d, J=12 Hz, 1, and dd, J=12 and 3.5 Hz, 1, $CH_2O$); $^{13}C$ NMR ($CDCl_3$), 65.8, 38.0, 35.5, 31.9, 31.3, 29.2, 27.4, 23.9, 22.5, 21.7, 18.0 ppm; MS calcd for $C_{11}H_{20}O$ 168.1514, found 168.1521.

Preparation of (2,2,6-trimethylbicyclo[4.1.0]hept-1-yl)carboxaldehyde (3)

To a solution of 50 mL of pyridine (0.62 mol) in 120 mL of $CH_2CL_2$ at 0° C. was added 32 g (0.32 mol) of $CrO_3$ in several portions. A solution of 6.72 g (40 mmol) of (2) in 5 mL of $CH_2Cl_2$ was added dropwise to the orange-brown mixture. The reaction mixture was allowed to warm to room temperature for 1 h and then was filtered through 50 g of Florisil (300 mL of $CH_2Cl_2$ wash). The filtrate was concentrated to give 6 g of a pale yellow oil, which was filtered through a column containing 200 g of silica gel with $CH_2Cl_2$. The 4.93 g (74%) of product was obtained as a colorless oil: IR (film) 2750 (CHO), 1700 (C=O), 1460, 1385, 1370, 1290, 1210, 1155, 1090, 1075, 995, 930, 910, 855 $cm^{-1}$; $^1H$ NMR ($CCl_4$) δ0.84 (d, J=5 Hz, 1, cyclopropyl H), 1.09–1.9 (m, 6, $CH_2$, and 1, cyclopropyl H), 1.03 (s, 3, $CH_3$), 1.13 (s, 3, $CH_3$), 1.44 (s, 3, $CH_3$), 9.64 (s, 1, CHO); $^{13}C$ NMR ($CDCl_3$) 202.9, 45.4, 36.5, 30.3, 29.9, 29.8, 29.6, 26.5, 22.4, 21.9, 17.0 ppm; MS calcd for $C_{11}H_{18}O$ 166.1358, found 166.1364.

Preparation of ethyl (E)-3-(2,2,6-trimethylbicyclo[4.1.0]hept-1-yl)-2-propenoate (4)

To a solution of 20 g (89 mmol) of triethyl phosphonoacetate in 30 mL of THF at −60° C. was added 61 mL of 1.44 M n-BuLi (88 mmol) in hexane. A solution of 7.4 g (44.5 mmol) of (3) in 10 mL of THF was then added. The mixture was warmed to room temperature and stirred for 16 h. $^1$H NMR analysis of a worked-up aliquot indicated that about 45% of the aldehyde remained unreacted. A second batch of the anion of triethyl phosphonoacetate was prepared from 20 g (89 mmol) of triethyl phosphonoacetate in 20 mL of THF at −60° C. and 60 mL of 1.44 M n-BuLi (86.4 mmol) in hexane and added to the reaction mixture. After stirring at room temperature for 6 h and storage at 0° C. for 60 h, the reaction mixture was diluted with 50 mL of $H_2O$ and extracted with 1:1 hexane/$Et_2O$ (3×100 mL). The organic layer was washed with brine (2×100 mL), dried ($Na_2SO_4$), and concentrated to give a light yellow oil. $^1$H NMR indicated that it still contained about 15% of unreacted aldehyde. The crude product was passed over 200 g of silica gel (5% $Et_2O$/hexane) to give 9.0 g of a colorless oil. To this oil dissolved in 25 mL of THF at 0° C. was added 16 mL of 0.5 M 9-BBN (8 mmol) in THF. The mixture was allowed to warm to room temperature over 30 min. After another 30 min, the mixture was concentrated to about 15 mL and diluted with 200 mL of $Et_2O$ before 0.45 mL (7.5 mmol) of ethanolamine was added. The mixture was kept at 0° C. for 1 h, filtered, concentrated, and chromatographed over 150 g of silica gel with 5% $Et_2O$/hexane. A total of 8.1 g (77%) of (4) was obtained as a colorless oil: IR (film) 2950, 1730 (C=O), 1650, 1460, 1375, 1320, 1289, 1180, 1050, 1000, 960, 870 cm$^{-1}$; $^1$H NMR (CDCl$_3$) δ0.48 and 0.62 (2 d, J=5 Hz, 2, cyclopropyl $CH_2$), 0.87, 0.97, and 1.12 (3 s, 9, $C_R$-16, $C_R$-17, and $C_R$-18 $CH_3$), 1.05–1.85 [m, 6, $(CH_2)_3$], 1.27 (t, J=7 Hz, 3, $CO_2CH_2\underline{CH}_3$), 4.15 (q, J=7 Hz, 2, $CO_2\underline{CH}_2CH_3$), 5.68 (d, J=15.5 Hz, 1, $C_R$-7 $\underline{HC}$=CH); 7.22 (d, J=15.5 Hz, 1, $C_R$-8 HC=$\underline{CH}$); MS calcd for $C_{15}H_{24}O_2$ 236.1776, found 236.1759.

Preparation of (E)-3-(2,2,6-trimethylbicyclo[4.1.0]hept-1-yl)-2-propenal (6)

A solution of 8.0 g (33.9 mmol) of (4) in 50 mL of $Et_2O$ was cooled in an ice bath while 100 mL of 1 M DIBAL (0.1 mol) in hexane was added over a 10-min period. The mixture was allowed to warm to room temperature over a 30-min period and stirred for 1 h. MeOH (5 mL) was added and the mixture was left to stand 1 h. The precipitated aluminum salts were filtered (800-mL ether wash). The filtrate was concentrated to give 7.2 g of a colorless oil, which was chromatographed on 120 g of silica gel with 1 L of 15% $Et_2O$/hexane and 1 L of 40% $Et_2O$/hexane to give 6.3 g (93% yield) of the alcohol (5): IR (film) 3350 (OH), 2950, 1670, 1460, 1385, 1365, 1210, 1110, 1080, 1020, 980 cm$^{-1}$; $^1$H NMR (CDCl$_3$) δ0.43 (m, 2, cyclopropyl $CH_2$), 0.87, 0.98, and 1.05 (3 s, 9, $C_R$-16, $C_R$-17, and $C_R$-18 $CH_3$), 1.0–1.8 [m, 6, $(CH_2)_3$], 2.33 (br, s, 1, OH), 4.12 (br, s, 2, $\underline{CH}_2$OH), 5.50 (m, 1, $C_R$-8 HC=$\underline{CH}$), 5.93 (d=16 Hz, 1, $C_R$-7 $\underline{HC}$=CH); MS calcd for $C_{13}H_{22}O$ 194.1671, found 194.1161.

To a solution of 6.0 g (31 mmol) of (5) in 50 mL of hexane and 150 mL of $CH_2Cl_2$ was added 80 g (0.92 mol) of activated $MnO_2$. The mixture was stirred at room temperature for 16 h and filtered. The filtrate was concentrated to give 5.1 g of colorless oil, which was chromatographed on 120 g of silica gel with 1 L of 5% EtOAc/hexane and 600 mL of 30% EtOAc/hexane to give 4.7 g of aldehyde (6), as a colorless oil, and 0.38 g of the unreacted alcohol (5), which was treated with 5 g (57 mmol) of $MnO_2$ in 20 mL of $CH_2Cl_2$ for 18 h to give another 0.3 g of (6). The total yield of (6) was 84%: IR (film) 2950, 2750 (CHO), 1710 (C=O) 1640, 1470, 1400, 1380, 1140, 990 cm$^{-1}$; $^1$H NMR (CDCl$_3$) δ0.63 and 0.83 (2 d, J=5 Hz, 2, cyclopropyl $CH_2$) 0.93, 1.03 and 1.23 (3 s, 9, $C_R$-16, $C_R$-17, and $C_R$-18 $CH_3$), 1.1–1.95 [m, 6, $(CH_2)_3$], 6.09 (dd, J=8 and 16 Hz, 1 $C_R$-8 HC=$\underline{CH}$), 7.23 (d, J=16 Hz, 1 $C_R$-7 $\underline{HC}$=CH), 9.63 (d, J=8 Hz, 1, CHO). The coupling constant (16 Hz) of the $7_R$ and $8_R$ vinylic protons indicates that these two protons are trans to each other; thus, the E configuration at this double bond was preserved.

Preparation of 1-(2,2,6-trimethylbicyclo[4.1.0]hept-1-yl)-1-buten-3-one (8)

To 5.5 mL (1.61 mmol) of 2.9 M MeMgBr in $Et_2O$ and 25 mL of anhydrous THF was added 2.8 g (14.6 mmol) of (6) in 5 mL of THF over a 15-min period. The reaction mixture was maintained at 20° C. for 30 min when TLC (1:1 $Et_2O$/hexane) indicated that reaction was complete. Saturated $NH_4Cl$ solution (2.5 mL) was added, and the reaction mixture was filtered (100-mL $Et_2O$ wash). The filtrate was concentrated to 3.4 g of a pale yellow oil, which was purified on a 150-g column of silica gel (20% EtOAc/hexane) to give 2.85 g (94%) of the pure secondary alcohol (7): IR (film) 3350 (OH), 2950, 1680, 1470, 1400, 1380, 1300, 1170, 1080, 990, 960, 880, cm$^{-1}$; $^1$H NMR (CDCl$_3$) δ0.42 and 0.53 (2 d, J=4 Hz, 2, cyclopropyl $CH_2$), 0.90, 0.98, and 1.07 (3 s, 9, $C_R$-16, $C_R$-17 and $C_R$-19 $CH_3$), 1.0–1.8 [m, 6, $(CH_2)_3$], 1.29 (d, J=6 Hz, 3, $C_R$-18 $CH_3$), 1.83 (s, 1, OH) 4.43 (q, J=6 Hz, 1, C$\underline{H}$OH), 5.53 (dd, J=6 and 16 Hz, 1, $C_R$-8 HC=$\underline{CH}$), 6.00 (d, J=16 Hz, 1, $C_R$-7 $\underline{HC}$=CH).

A mixture of 2.8 g (13.4 mmol) of (7) and 30 g (0.34 mol) of activated $MnO_2$ in 50 mL of $CH_2Cl_2$ and 20 mL of hexane was stirred at room temperature for 16 h. After filtration (200 mL ether rinse) and concentration, chromatography over 100 g of silica gel with 10% and 20% EtOAc/hexane gave 2.0 g (72%) of (8), as a colorless oil: IR (film) 2950, 1670 (C=O), 1620, 1450, 1360, 1250, 990 cm$^{-1}$; $^1$H NMR (CDCl$_3$) δ0.55 and 0.72 (2 d, J=5 Hz, 2, cyclopropyl $CH_2$), 0.90, 1.00, and 1.16 (3 s, 9, $C_R$-16, $C_R$-17, and $C_R$-18 $CH_3$), 1.10–1.90 [m, 6, $(CH_2)_3$], 2.27 (s, 3, $COCH_3$), 6.03 (d, J=16 Hz, 1, $C_R$-8 HC=$\underline{CH}$), 7.17 (d, J=16 Hz, 1, $C_R$-7 $\underline{HC}$=CH); MS calcd for $C_{14}H_{22}O$ 206.1671, found 206.1675. In addition 0.6 g of (7) was recovered.

Preparation of (E)-1-(4-carbethoxyphenyl)-2-methyl-4-(2,2,6-trimethylbicyclo[4.1.0]hept-1-yl)-1,3-butadiene (10, R$^1$=Et)

To a solution of 3.6 g (12 mmol) of diethyl p-carbethoxybenzylphosphonate (9) in 10 mL of THF at −60° C. was added 8.2 mL of 1.4 M n-BuLi (11.5 mmol) in hexane. The cooling bath was removed and 1.2 g (5.8 mmol) of (8) in 6 mL of THF was added. The mixture was stirred at room temperature for 16 h. The reaction mixture was diluted with 50 mL of $H_2O$ and extracted with 10% EtOAc/hexane (2×50 mL). The organic layer was washed with brine (2×100 mL), dried ($Na_2SO_4$), and concentrated to give 3.5 g of a yellow oil.

Chromatography on 100 g of silica gel (5% EtOAc/hexane) gave 1.5 g of a product mixture, which showed six peaks on LC analysis (Radialpak B, 1% Et$_2$O/hexane, 2 mL/min, 260 nM): $t_R$ 7.6 (1%), 8.2 (1.5%), 10.2 (75.5%), 11.6 (20%), 14.2 (1%), and 17.3 min (1%). Multiple passes on preparative LC (0.4% Et$_2$O/hexane) using the recycle technique afforded 0.8 g (39% yield) of the 7$_R$E,9$_R$Z isomer of (10) and 0.33 g (16% yield) of the desired isomer (10) as light yellow viscous oils. 7$_R$E,9$_R$E-Isomer (10): LC (Radialpak B, 1% Et$_2$O/hexane, 2 mL/min, 260 nm) $t_R$ 11.6 min (>99%); LC (Radialpak A, 5% H$_2$O/MeOH, 2 mL/min, 260 nm), $t_R$ 9.8 min (100%); IR (film) 2950, 1730 (C=O), 1610, 1280, 1110, 880, 770 cm$^{-1}$; UV (EtOH) $\lambda_{max}$ 390 nm ($\epsilon$2.54×10$^4$), 232 (1.12×10$^4$); MS calcd for C$_{24}$H$_{32}$O$_2$ 352.2402, found 352.2397.

The compounds of formula (A) wherein X represents a substituted butadienyl group may be prepared by the following reaction scheme:

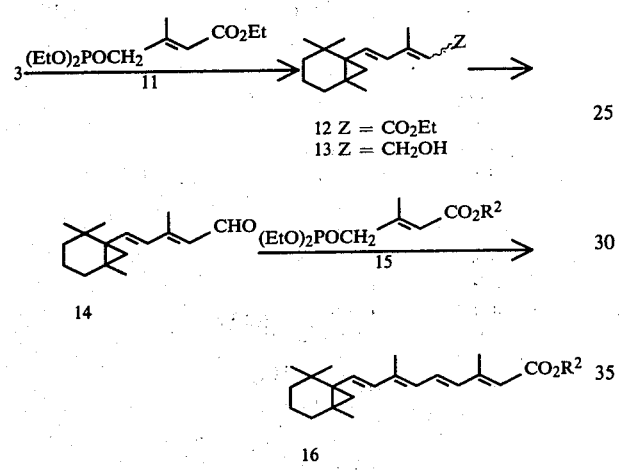

where R$^2$ is as defined previously.

This scheme was used to make ethyl (E)-5,6-methano-5,6-dihydroretinoate as follows. The abbreviations have the same meanings as above:

(2,2,6-Trimethylbicyclo[4.1.0]hept-1-yl) carboxaldehyde (3) was prepared as described above.

Preparation of (4E)-3-methyl-5-(2,2,6-trimethylbicyclo[4.1.0]hept-1-yl)2,4-pentadien-1-ol (13)

A solution of 26 g (98 mmol) of diethyl (E)-3-(carbethoxy)-2-methyl-2-propenylphosphonate (11) in 15 mL of THF was cooled to −78° C., and 62.5 mL of a 1.46 M solution of n-BuLi (91 mmol) in hexane was added over a 20-min period, followed by 4.7 g (28.3 mmol) of (3) in 5 mL of THF. The reaction mixture was stirred at room temperature for 48 h, diluted with 100 mL of H$_2$O, and extracted with hexane (3×50 mL). The combined hexane extract was washed with brine (2×100 mL), dried (Na$_2$SO$_4$), and evaporated to give 10.3 g of a light yellow oil, which was chromatographed on 350 g of silica gel with 5% Et$_2$O/hexane. A total of 6.0 g (77% yield) of a 1:4 mixture by $^1$H NMR of the 2Z- and 2E-isomers of (12) was obtained as a colorless oil: IR (film) 2900, 1720, 1640, 1620, 1450, 1370, 1240, 1160, 1060, 980, 880 cm$^{-1}$; $^1$H NMR (CDCl$_3$) 0.47, 0.53 (2 d, J=5 Hz, 2, cyclopropyl CH$_2$), 0.87, 0.95, 1.08 (3 s, 9, C$_R$-16, C$_R$-17, and C$_R$-18 CH$_3$), 1.0–1.75 [m, 6, (CH$_2$)$_3$], 1.27 (t, J=7 Hz, 3, CO$_2$CH$_2$CH$_3$), 2.00 and 2.30 (2 s, 3, 2Z and 2E C=CCH$_3$, respectively), 4.16 (q, J=7 Hz, 2, CO$_2$CH$_2$CH$_3$), 5.5–5.75 (m, 1, C=CHCO$_2$), 6.32 and 6.37 (2 d, J=16 Hz, 1, 2E and 2Z C-5 HC=CH, respectively), 6.1 and 7.52 (2 d, J=16 Hz, 1, 2E and 2Z C-4 HC=CH, respectively). The assignments agree closely with those reported from methyl (2E,4E)- and (2Z,4E)-3-methyl-5-(2,6,6-trimethyl-1-cyclohexen-1-yl)-2,4-pentadienoates.

A 5.8-g (21 mmol) portion of diene ester (12) was dissolved in 100 mL of Et$_2$O cooled to 0° C., and treated with 45 mL (45 mmol) of a 1 M solution of DIBAL in hexane over a 15-min period. The mixture was warmed up to room temperature over 30 min, at which time TLC (1:1 hexane/Et$_2$O) indicated that reaction was complete. MeOH (5 mL) was added dropwise to the reaction mixture, with cooling, to decompose excess reagent, and the resultant white precipitate was filtered (500-mL ether wash). The ethereal solution was concentrated to give 4.88 g of a colorless, viscous oil, which was purified on 150 g of silica gel with 25% Et$_2$O/hexane to give 4.2 g of a mixture of the 2E- and 2Z-isomers of (13), followed by 0.5 g of the pure 2E,4E-isomer (96% total yield): IR (film) 3250 (OH), 2900, 1470, 1390, 1370, 1090, 980 cm$^{-1}$; $^1$H NMR (CDCl$_3$) $\delta$0.33–0.55 (m, 2, cyclopropyl CH$_2$); 0.83, 0.94, 1.00 (3 s, 9, C$_R$-16, C$_R$-17, and C$_R$-18 CH$_3$), 1.05–1.75 [m, 6, (CH$_2$)$_3$], 1.77 (s, 3, C=CCH$_3$), 4.21 (d, J=7 Hz, 2, CH$_2$OH), 5.53 (t, J=7 Hz, 1, C=CH), 5.93 (s, 2, C$_R$-7 and C$_R$-8 HC=CH); MS calcd for C$_{16}$H$_{26}$O 234.1984, found 234.1975.

Preparation of (E)-3-methyl-5-(2,2,6-trimethylbicyclo[4.1.0]hept-1-yl)-2,4-pentadienal (14)

A mixture of 3.5 g (25 mmol) of the alcohol mixture (13) [7:1 (2E)/(2Z)/ by $^1$H NMR] and 60 g (0.69 mol) of activated MnO$_2$ (Alfa) in 50 mL of hexane and 150 mL of CH$_2$Cl$_2$ was stirred at room temperature for 60 h and then filtered through Celite (300 mL of CH$_2$Cl$_2$ wash). The filtrate and washings were concentrated to give a colorless oil, which was chromatographed on 120 g of silica gel with 25% Et$_2$O/hexane to give 2.75 g (79% yield) of a mixture of aldehydes. The aldehydes were separated by two passes on preparative LC (4% Et$_2$O/hexane) to afford 1.6 g (46% yield) of the pure 2E-isomer (14) as a colorless oil and 0.47 g (14% yield) of its isomer, also a colorless oil. 2E,4E-Isomer (14): IR (film) 2950, 2750 (CHO), 1720 (C=O), 1680, 1640, 1450, 1210, 1110, 980 cm$^{-1}$; $^1$H NMR (CDCl$_3$) $\delta$0.57, 0.72 (2 d, J=6 Hz, 2, cyclopropyl CH$_2$), 0.92, 1.00, 1.15 (3s, 9, C$_R$-16, C$_R$-17, and C$_R$-18 CH$_3$), 1.1–1.9 [m, 6, (CH$_2$)$_3$], 2.35 (d, J=1 Hz, 3, C=CCH$_3$), 5.98 (d, J=8 Hz, 1, C=CH), 6.19 (d, J=16 Hz, 1 C$_R$-7 HC=CH), 6.70 (d, J=16 Hz, 1, C$_R$-8 HC=CH), 10.18 (d, J=8 Hz, 1, CHO); MS calcd for C$_{16}$H$_{24}$O 232.1827, found 232.1844.

Preparation of ethyl (E)-5,6-methano-5,6-dihydroretinoate (16)

A solution of 2.11 g (8 mmol) of phosphonate (15) (R$^2$=Et) in 4 mL of THF at −78° C. was treated with 5 mL of a 1.46 M solution of n-BuLi (7.3 mmol) in hexane. The solution was stirred for 10 min; then 1.5 g (6.46 mmol) of (14) in 5 mL of THF was added. The mixture was warmed up to room temperature over a period of 1 h. After another 2 h, TLC (1:1 hexane/Et$_2$O) indicated that the reaction was complete.

The reaction mixture was diluted with 50 mL of brine and extracted with hexane (3×50 mL). The combined hexane extracts were washed with brine (3×50 mL), dried (Na$_2$SO$_4$), and concentrated to give 30 g of a yellow viscous oil, which was passed over a precolumn of 120 g of silica gel with 25% Et$_2$O/hexane to give 1.6 g of a very pale yellow oil. LC analysis (Radialpak B, 0.5% Et$_2$O/hexane, 2 mL/min, 260 nm) revealed four peaks: t$_R$ 13.4 (21%), 15.8 (shoulder, 2%), 16.7 (13%), and 19.5 min (64%). The three major isomers were separated by multiple passes on preparative LC (0.5% Et$_2$O/hexane, 1% EtOAc/hexane). A total of 0.8 g (36% yield) of the desired all-E-isomer (16) was obtained as a very pale yellow oil, which gradually crystallized on standing: mp 57°–58° C.; LC (Radialpak B, 0.5% Et$_2$O/hexane, 2.0 mL/min, 260 nm) t$_R$ 16.7 (0.1%) and 19.5 min (99.9%); LC (Radialpak A, 5% H$_2$O/MeOH, 2.0 mL/min, 260 nm) t$_R$ 12.9 min (100%); IR (film) 2900, 1720 (C=O), 1600, 1450, 1350, 1250, 1150, 1050, 980, 880, 830 cm$^{-1}$; UV (EtOH) $\lambda_{max}$ 344 nm ($\epsilon$4.8×10$^4$), 234 (4.0×10$^3$); MS calcd for C$_{23}$H$_{34}$O$_2$ 342.2559, found 342.2540.

The 5,6-methano-5,6-dihydroretinoids of formula (A) may be used topically or systemically as chemopreventive agents and in the treatment, amelioration, or prevention of the skin disorders and rheumatic illnesses for which retinoic acid and other retinoids are useful. In this regard, they may be used for therapy in animals, including humans, of premalignant epithelial cell lesions, as a prophylaxis against tumor promotion in epithelial cells and treatment for dermatoses such as icthyoses, follicular disorders, benign epithelial disorders, and other proliferative skin diseases (nonmalignant conditions of the skin that are characterized by epidermal cell proliferation or incomplete cell differentiation) such as acne, psoriasis, eczema, atopic dermatitis, nonspecific dermatitis and the like. When used for such treatments they will usually be formulated with a pharmaceutically acceptable liquid, semi-solid, or solid carrier. A pharmaceutically acceptable carrier is a material that is nontoxic and generally inert and does not affect the functionality of the active ingredients adversely. Such materials are well known and include those materials sometimes referred to as diluents or vehicles in the pharmaceutical formulation art. The carrier may be organic or inorganic in nature. Examples of pharmaceutically acceptable carriers that may be used to formulate the retinoids are water, gelatin, lactose, starch, mineral oil, cocoa butter, dextrose, sucrose, sorbitol, mannitol, gum acacia, alginates, cellulose, talc, magnesium stearate, polyoxyethylene sorbitan monolaurate, and other commonly used pharmaceutical carriers. In addition to the retinoid and carrier the formulation may contain minor amounts of additives such as flavoring agents, coloring agents, thickening or gelling agents, emulsifiers, wetting agents, buffers, stabilizers, and preservatives such as antioxidants.

For topical administration the retinoids are conveniently provided in the form of ointments, tinctures, creams, solutions, lotions, sprays, suspensions, and the like. The amount of retinoid in such topical formulations will normally be in the range of about 0.01 to about 1% by weight. For enteral (oral or rectal) administration the retinoids will typically be formulated as tablets, capsules, dragees, syrups, solutions, or suppositories. For parenteral administration the retinoids will be formulated as injectable solutions or suspensions.

The dosages and dosage regimen in which the retinoids are administered will vary according to the dosage form, mode of administration, the condition being treated, and particulars of the patient being treated. They will, of course, be administered in chemopreventive (tumor promotion inhibiting) amounts or therapeutically effective amounts, as the case may be. For adult humans chemopreventive amounts will usually be about 0.01 mg to 10.0 mg daily given in one or more doses. Oral doses will generally be less than topical doses and doses for treating skin disorders will typically be less than doses administered for chemoprevention. The dose for treating skin disorders will be on the order of, but normally less than, the dose of retinoic acid prescribed for the disorder.

The usefulness of the invention compounds as chemopreventive agents for treating humans was demonstrated by testing ethyl (E)-5,6-methano-5,6-dihydroretinoate and (E)-1-(4-carbethoxyphenyl)-2-methyl-4-(2,2,6-trimethylbicyclo[4.1.0]hept-1-yl)-1,3-butadiene in the ornithine decarboxylase (ODC) assay, Verma, A. K. and Boutwell, R. K.; Cancer Res (1977) 37:2196-2201, and the tracheal organ culture assay, Newton, D. L.; Henderson, W. R.; and Sporn, M. B.; Cancer res (1980) 40:3413-3425. The ODC assay measures a compound's effect on the prevention of the induction of ODC. The tracheal organ culture assay measures a compound's ability to reverse keratinization. For comparison purposes retinoic acid was also tested by these assays.

The ODC assay is carried out as follows. Female Charles River CD-1 mice from Charles River Breeding Laboratories, Wilmington, Mass., are used (age 7 to 9 weeks). The dorsal hair of the mice is shaved 1 to 2 days before testing, and only mice showing no hair regrowth are used. A single dose of 12-O-tetradecanoylphorbol-13-acetate (TPA) (10.5 $\mu$g, 17 nmol) in 0.2 mL of acetone is applied topically to the back of each mouse. The test compound, at one of three dose levels (1.7, 17, and 170 nmol), dissolved in 0.2 mL of acetone is applied 1 hour before the TPA treatment to the test groups; the control group is treated with acetone alone. The mice are killed by cervical dislocation five hours after TPA treatment. Determinations are done in triplicate.

The epidermis is obtained from the sacrificed animals. To obtain sufficient material, the dorsal skins from 2 to 3 mice in each treatment group are pooled. The depilatory agent Nudit ® (Helena Rubinstein, New York) is applied to the shaved area of the skin; after 5 minutes, it is washed off thoroughly with cold tap water. Then the skin is excised and plunged immediately into ice-cold water; it is then placed in a 55° C. water bath for 30 seconds and reimmersed in ice-cold water for at least another 30 seconds. The skin is placed epidermic side up on a cold plate, and the epidermis is scraped off with a razor blade. The pooled epidermal sheets are homogenized (Polytron PT-10 homogenizer) at 0° to 4° C. for 15-20 seconds in 50 mM sodium phosphate buffer (pH 7.2) containing 0.1 mM pyridoxal phosphate and 0.1 mM ethylenediaminetetraacetic acid (EDTA), at a volume of 1 mL/skin.

The supernatant fraction remaining after centrifugation of the homogenate at 10,000×g for 30 seconds at 0° C. is used for the enzyme assay. Enzyme activity is determined using the microassay for ODC as described by Verma and Boutwell to measure the release of $^{14}$CO$_2$ from DL-[1-$^{14}$C]-ornithine (58 mCi/mmol) after incubation with the 10,000×g supernatant. The incubations are carried out by decanting, with a Pasteur pipette, 100 μL of the supernatant containing 100 to 120 μg of protein into two or three 15-mL Corex tubes in a shaking water bath at 37° C. The assay mixture in the tubes consists of 50 μL of 100 mM sodium phosphate buffer (pH 7.2), 10 μL of 4 mM pyridoxal phosphate, 40 μL of 25 mM dithiothreitol, and 1 μL of 0.1 M EDTA. The center wells in the tubes are filled with 200 μL of a 2:1 solution (v/v) of ethanolamine:2-methoxy-ethanol. The reaction is started by adding 50 μL of substrate (0.5 μCi of DL-[1-$^{14}$C]-ornithine in 2 mM cold ornithine) at 1-minute intervals by injection to each of the stoppered tubes. Incubations are routinely carried out at 37° C. for 30 to 60 minutes. The reaction is stopped by addition of 0.5 ml of 2 M citric acid, and incubation is continued for an additional hour without heating to ensure complete absorption of $^{14}CO_2$.

Radioactivity is measured using a toluene-based scintillant (4 g of PPO and 50 mg of POPOP/L of toluene) in a Beckman LS-250 liquid scintillation counter. Enzyme activity is determined in triplicate and expressed as nanomoles of $CO_2$ released in 30 minutes per milligram of protein. Enzyme activity is linear for the protein concentration used. The protein concentrations of the epidermal extracts are determined by the Lowry procedure, using bovine serum albumin as the standard.

The tracheal organ culture assay is carried out as follows. Tracheas are taken from hamsters that are in very early stages of vitamin A deficiency and placed in organ culture. At the time of culture, the animals are still gaining weight; the tracheal epithelium is generally low columnar or cuboidal, with only occasional patches of squamous metaplasia. Each trachea is opened from the larynx to the carina along the membranous dorsal wall and cultured in a serum-free medium (CMRL-1066; with crystalline bovine insulin, 0,1 μg/ml; hydrocortisone hemisuccinate, 0.1 μg/ml; glutamine, 2 mM; penicillin, 100 units/ml; and streptomycin, 100 μg/ml, added). Cultures are gassed with 50% oxygen, 45% nitrogen, and 5% $CO_2$. The culture dishes are rocked at 35.5–36.0 degrees to allow the tracheas contact with both gas and medium. All tracheas are grown in medium containing no retinoid for the first 3 days. At the end of 3 days, some tracheas are harvested; almost all of these tracheas have significant squamous metaplasia, and approximately 60% have keratinized lesions. The remaining tracheas are then divided into different groups which are treated with either: (1) retinoid dissolved in dimethylsulfoxide (final concentration of DMSO in culture medium is never greater than 0.1%) or (2) an equivalent amount of DMSO alone. Culture medium is changed three times a week, and all of the remaining tracheas are harvested at the end of 10 days in culture. Tracheas are fixed in 10% buffered formalin and embedded in paraffin. Cross sections of five micrometers are made through the mid-portion, stained with hematoxylin and eosin, and then scored with a microscope for the presence of keratin and keratohyaline granules, both of which are found in approximately 90% of control cultures that recycled no retinoid for the entire 10 day culture period. Retinoids are scored as "inactive" if both keratin and keratohyaline granules are seen; they are scored as "active" if neither keratin nor keratohyaline granules are seen, or if keratohyaline granules alone are absent.

The table below gives the results of these tests.

| | Reversal of Keratinization in Hamster Tracheal Organ Culture | | Inhibition of Induction of Ornithine Decarboxylase by 12-O—Tetradecanoyl-phorbol-13-acetate in Mouse Skin | |
|---|---|---|---|---|
| | Conc (M) | Active/Total Cultures (%) | Dose (nmol) | % Inhibition of Control |
| ethyl (E)—5,6-methano-5,6-dihydroretinoate | $10^{-8}$ | 7/7 (100) | 17 | 70 |
| | $10^{-9}$ | 11/14 (79) | | |
| | $10^{-10}$ | 7/14 (50) | | |
| | $10^{-11}$ | 2/7 (29) | | |
| (E)—1-(4-carb-ethoxyphenyl)-2-methyl-(2,2,6-trimethylbicyclo-[4.1.0]hept-1-yl)-1,3-butadiene | $10^{-8}$ | 7/7 (100) | 17 | 80 |
| | $10^{-9}$ | 10/13 (77) | | |
| | $10^{-10}$ | 4/14 (29) | | |
| | $10^{-11}$ | 2/7 (29) | | |
| (E)—retinoic acid | $10^{-8}$ | 236/236 (100) | 1.7 | 87–91 |
| | $10^{-9}$ | 419/474 (88) | | |
| | $10^{-10}$ | 134/256 (52) | | |

These results show that the 5,6-methano-5,6-dihydroretinoids of the invention possess antitumor promotion activity.

Modifications of the above described modes for carrying out the invention that are obvious to those of skill in the fields of organic chemistry, pharmaceuticals, and/or medicine are intended to be within the scope of the following claims.

We claim:

1. A compound of the formula

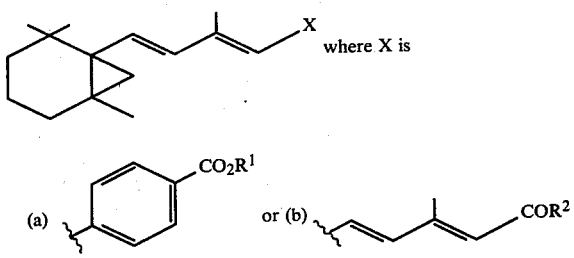

where X is and $R^1$ is hydrogen, alkyl or aryl and $R^2$ is hydroxyl alkoxy or $NR^3R^4$ where $R^3$ is hydrogen, alkyl, or aryl and $R^4$ is alkyl or aryl and the 13-cis isomers of those compounds where X is (b).

2. The compound of claim 1 wherein $R^1$ is hydrogen, alkyl of 1 to 8 carbon atoms or aryl of 6 to about 15 carbon atoms and $R^2$ is hydroxyl, alkoxy of 1 to about 8 carbon atoms or $NR^3R^4$ where $R^3$ is hydrogen, alkyl of 1 to about 8 carbon atoms substituted with 0 or 1 hydroxy groups or aryl of 6 to about 15 carbon atoms and $R^4$ is alkyl of 1 to about 8 carbon atoms substituted with 0 or 1 hydroxy groups or aryl of 6 to about 15 carbon atoms.

3. The compound of claim 1 where X is

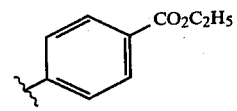

4. The compound of claim 1 where X is

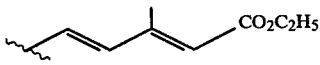

5. A pharmaceutical composition comprising a pharmaceutically effective amount of the compound of claim 1, 2, 3, or 4 combined with a pharmaceutically acceptable carrier.

6. A chemopreventive composition for inhibiting tumor promotion is epithelial cells in a living animal comprising a tumor promotion inhibiting amount of the compound of claim 1, 2, 3, or 4 combined with a pharmaceutically acceptable carrier.

7. A therapeutic composition for treating a nonmalignant skin disorder comprising a therapeutically effective amount of the compound of claim 1, 2, 3, or 4 combined with a pharmaceutically acceptable carrier.

8. A method of inhibiting tumor promotion in epithelial cells of a living animal comprising administering a tumor promotion inhibiting amount of the compound of claim 1, 2, 3, or 4 to the animal.

9. The method of claim 8, wherein the animal is human.

10. A method of treating a living animal for a nonmalignant skin disorder comprising administering a therapeutically effective amount of the compound of claim 1, 2, 3, or 4 to the animal.

11. The method of claim 10 wherein the compound is administered topically to the affected area of the skin.

12. The method of claim 10 wherein the animal is human.

* * * * *